US 6,659,983 B2

(12) United States Patent
Crawford et al.

(10) Patent No.: US 6,659,983 B2
(45) Date of Patent: Dec. 9, 2003

(54) NEEDLE ASSEMBLY

(75) Inventors: Jamieson William Maclean Crawford, New York, NY (US); Stefanie Livanos, Bethlehem, PA (US)

(73) Assignee: Becton Dickinson and Company, Franklin Lakes, NJ (US)

(*) Notice: Subject to any disclaimer, the term of this patent is extended or adjusted under 35 U.S.C. 154(b) by 168 days.

(21) Appl. No.: 10/054,287

(22) Filed: Nov. 13, 2001

(65) Prior Publication Data

US 2002/0103465 A1 Aug. 1, 2002

Related U.S. Application Data

(60) Provisional application No. 60/259,874, filed on Jan. 5, 2001.

(51) Int. Cl.⁷ .................................................. A61M 5/32
(52) U.S. Cl. ........................ 604/192; 604/177; 604/272
(58) Field of Search ............................. 604/93.01, 110, 604/116, 117, 162, 164.04, 164.07, 164.08, 165.08, 174, 177, 192, 197, 198, 263, 264, 272

(56) References Cited

U.S. PATENT DOCUMENTS

| | | |
|---|---|---|
| 5,147,327 A | 9/1992 | Crawford et al. |
| 5,330,438 A | 7/1994 | Gollobin et al. |
| 5,549,571 A | 8/1996 | Sak |
| 5,879,337 A | 3/1999 | Kuracina et al. |

FOREIGN PATENT DOCUMENTS

| | | |
|---|---|---|
| WO | WO 92/11885 | 7/1992 |
| WO | WO 92/20281 | 11/1992 |
| WO | WO 93/01851 | 2/1993 |
| WO | WO 98/42393 | 10/1998 |

*Primary Examiner*—Manuel Mendez
*Assistant Examiner*—Mark K Han
(74) *Attorney, Agent, or Firm*—Nanette S. Thomas, Esq.

(57) ABSTRACT

An automatically shieldable blood collection set is provided. The blood collection set includes a needle assembly having a hub to which a needle cannula is fixedly attached. The needle hub includes a fin formed with a latch. A safety shield is telescoped relative to the hub and the needle cannula and can be moved from a proximal position where the needle cannula is exposed to a distal position where the needle cannula is safely shielded. The latch on the fin releasably engages the shield when the shield is in the proximal position. A spring is provided between the shield and the hub to propel the shield distally relative to the hub and into surrounding relationship with the needle cannula in response to movement of the latch.

7 Claims, 2 Drawing Sheets

NEEDLE ASSEMBLY

This application claims the benefit of provisional application No. 60/259,874 filed Jan. 5, 2001.

BACKGROUND OF THE INVENTION

1. Field of the Invention

The subject invention relates to a blood collection set having a needle cannula and a shield that can be driven forwardly to safely shield the needle cannula.

2. Description of the Related Art

A prior art blood collection set includes a small diameter needle cannula having a pointed distal end and a proximal end mounted to a thermoplastic hub. Portions of the blood collection set near the hub may be provided with a pair of flexible wings. The wings can be folded into face-to-face engagement with one another to facilitate digital manipulation of the small needle cannula. The wings then can be folded away from one another and taped into face-to-face engagement with the skin of the patient near a puncture site. The prior art blood collection set further includes a flexible plastic tube that has one end connected to the hub and an opposed end connected to a fitting. The fitting can be placed in communication with a reservoir to which collected blood may be directed.

The needle cannula of the prior art blood collection set typically is shielded prior to and after use to prevent accidental sticks. Needle shields used with prior art blood collection sets have taken many forms. Typically, a prior art blood collection set is packaged with a rigid tubular cap telescoped over the needle cannula to prevent accidental sticks prior to use. This tubular cap is removed from the needle cannula immediately prior to use of the blood collection set. Most prior art blood collection sets further include a second shield that is telescoped over the needle cannula and hub. The second shield may include at least one slot through which wings of the prior art hub may extend. Thus, the medical technician who uses the prior art blood collection set will hold the wings of the needle hub in one hand and the shield in the other hand after removing the needle cannula from the patient or blood donor. The wings then are slid proximally relative to the shield, thereby drawing the needle cannula into the shield. Some prior art shields are configured to engage the wings when the needle cannula has been shielded to make a re-exposure of the needle cannula difficult.

The digital manipulation that is required to shield the used needle cannula of a prior art blood collection set creates the potential for generating the accidental needle stick that the shield is intended to avoid. In particular, it is undesirable to rely upon a shielding that requires two hands to be moved in opposite directions in proximity to the point of a used needle cannula. Accordingly, the inventors herein have recognized the desirability of providing an automatically shieldable needle cannula for a blood collection set.

SUMMARY OF THE INVENTION

The subject invention relates to a blood collection set which comprises a needle cannula having a proximal end, a pointed distal end and a lumen extending therebetween.

The blood collection set further includes a hub that may be molded from a thermoplastic material. The hub includes a proximal end, a distal end and a passage extending continuously therebetween. The distal end of the hub is securely mounted to the proximal end of the needle cannula. Thus the lumen through the needle cannula communicates with the passage through the hub. The hub includes at least one fin and/or wing extending outwardly therefrom. The fin and/or wing are provided to facilitate gripping and manipulation of the needle assembly.

The blood collection set may further include a length of flexible tubing having opposed proximal and distal ends. The distal end of the flexible tubing may be connected to the proximal end of the hub such that the lumen through the needle cannula and the passage through the hub both communicate with the passage through the flexible tubing. The flexible tubing further includes a proximal end that may be connected to a fitting. The fitting may comprise a needle cannula that enables the blood collection set to be placed in communication with a reservoir for receiving a sample of blood. The tubing and the fitting may be of conventional design.

The blood collection set may further include a substantially rigid generally tubular safety cap mounted over the needle cannula for protection against accidental needle sticks prior to use of the blood collection set. The safety cap may include a proximal end that is frictionally engaged with the hub. The rigid tubular safety cap may be removed immediately prior to use of the blood collection set.

The blood collection set further includes a safety shield that is movable along the hub and cannula from a proximal position, where the needle cannula is exposed, to a distal position, where the needle cannula is safely shielded. The shield may further include its own fin and/or wing that can be aligned with a corresponding fin and/or wing projecting from the hub. Biasing means are provided between the shield and the hub for urging the shield to the distal position. The biasing means may be a coil spring that surrounds a portion of the hub.

The needle assembly may further include a latch formed on the fin or wing projecting outwardly from the hub. The latch may include a locking portion for releasably engaging a portion of the shield when the shield is in its proximal position. The latch may further include an actuating portion that can be actuated digitally for releasing the locking portion from the shield and permitting the shield to be propelled to the distal position by the biasing means. The locking portion of the latch may engage a locking recess formed in a fin or wing that projects outwardly from the shield.

DETAILED DESCRIPTION

Figure 1:
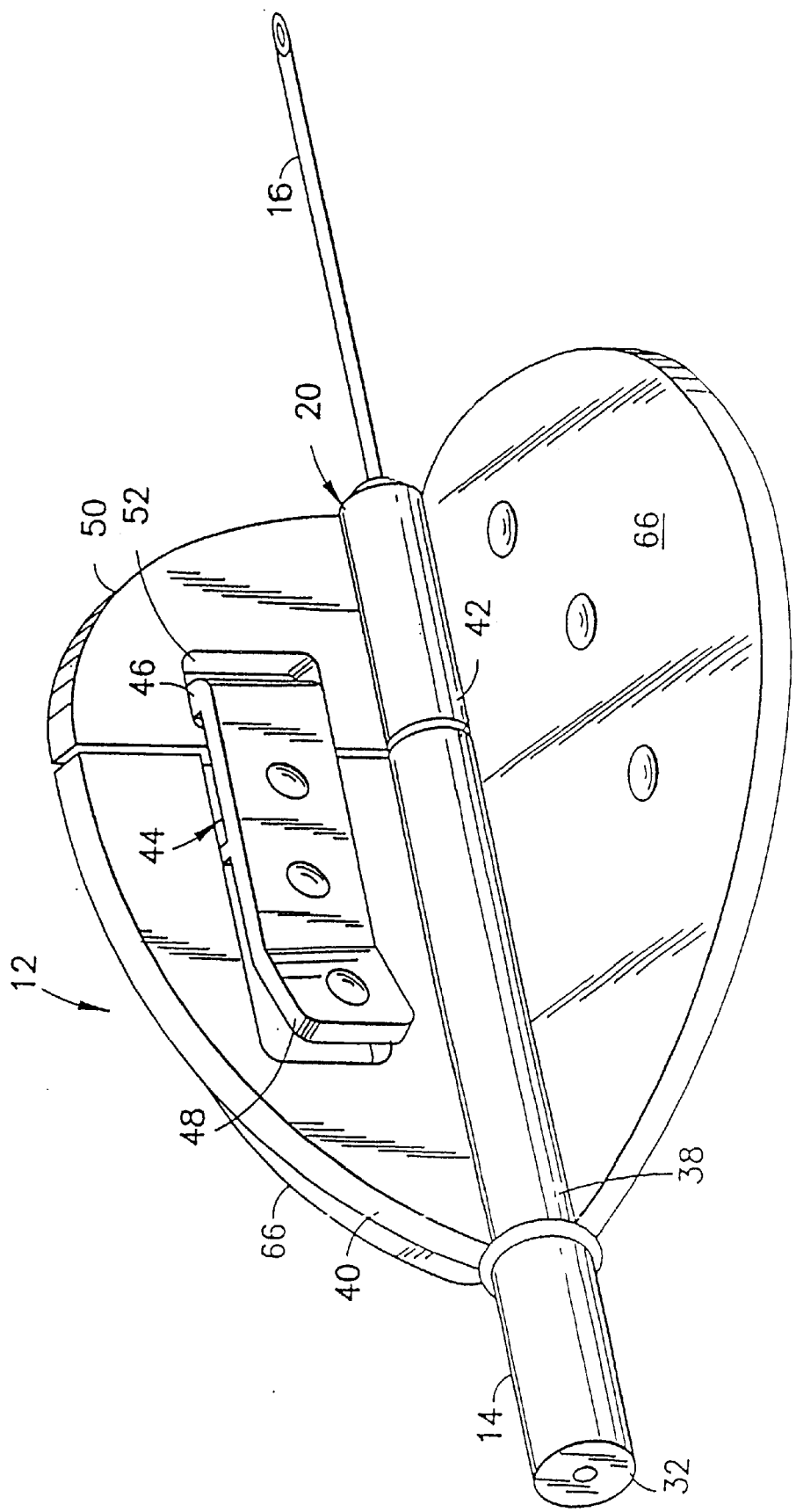
FIG. 1 is a perspective view of a blood collection set in accordance with the subject invention with the needle exposed.
Figure 2:
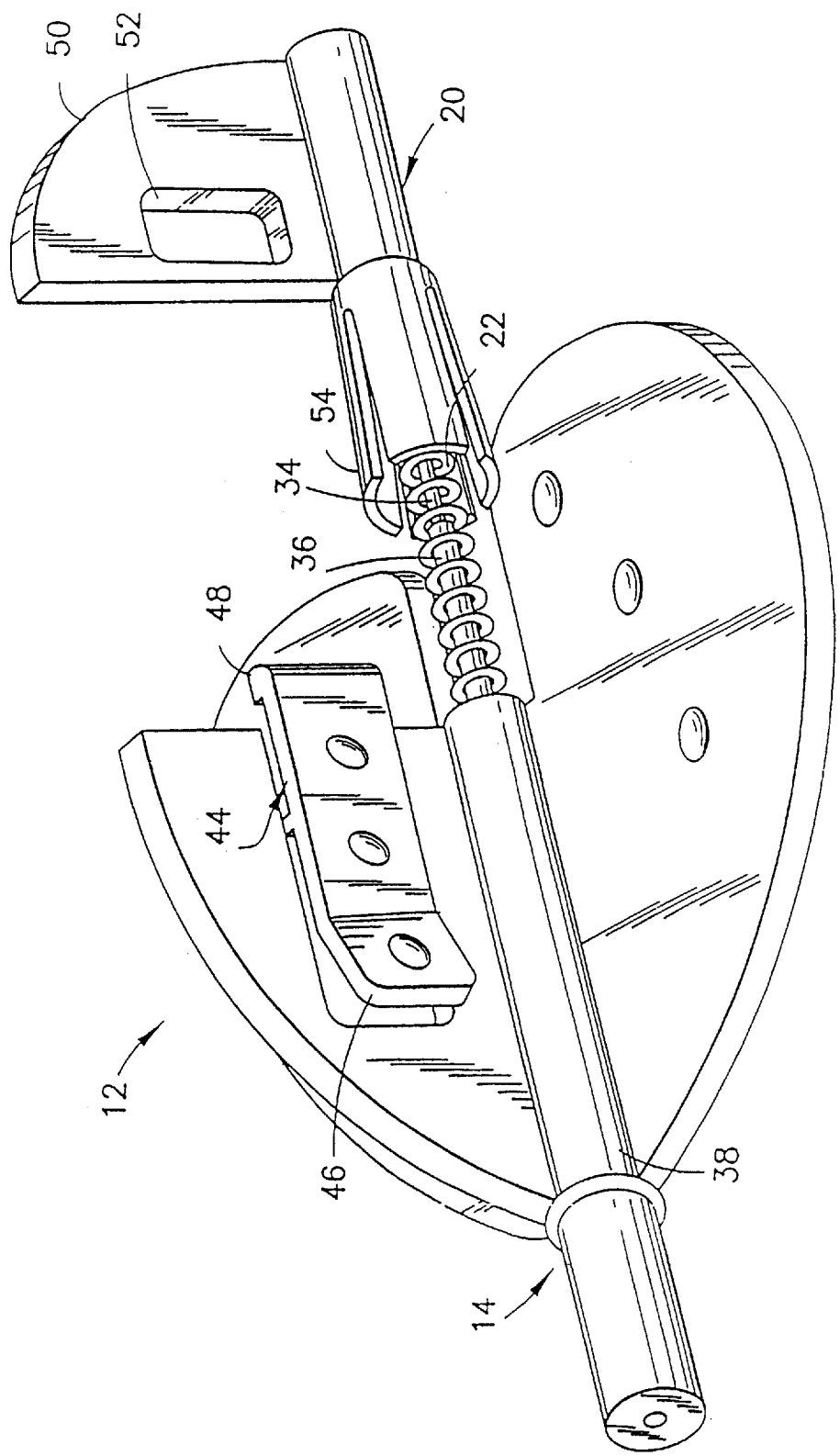
FIG. 2 is a perspective view of the blood collection set of FIG. 1, but with the needle in its shielded condition.

A needle assembly in accordance with the subject invention is identified generally by the numeral 12 in FIGS. 1 and 2. Needle assembly 12 includes a needle hub 14, a needle cannula 16, a protective cap (not shown), a shield 20 and a spring 22. Needle hub 14 has a proximal end 32 and a distal end 34. Additionally, needle hub 14 includes tubular inner and outer walls 36 and 38 which are disposed in spaced concentric relationship to one another. Needle cannula 16 is securely mounted to inner wall 36 of hub 14. Outer wall 38 of hub 14 is characterized by a pair of oppositely directed wings 66. Additionally, a dorsal fin 40 extends rigidly from outer wall 38 at a location between wings 66. Dorsal fin 40 extends from proximal end 32 toward distal end 34. However, outer wall 38 of hub 14 is provided with a slot 42 extending from distal end 34 to dorsal fin 40.

A latch 44 is formed on dorsal fin 40. Latch 44 includes an actuator end 46 and a locking end 48. Actuator end 46 projects angularly from dorsal fin 40 and enables resilient deflection of latch 44 relative to dorsal fin 40. Locking end 48 projects distally beyond dorsal fin 40.

Shield 20 includes a proximal end that is telescoped between inner and outer walls 36 and 38 of hub 14. Additionally, shield 20 includes a dorsal fin 50 dimensioned to be engaged in slot 42 of outer wall 38 of hub 14. Dorsal fin 50 of shield 20 is provided with a locking recess 52 disposed and dimensioned to be engaged by locking end 48 of latch 44. Spring 22 is stored in a compressed state between proximal end 32 of hub 14 and shield 20 in the condition shown in FIG. 12.

Needle assembly 12 is used in the conventional manner. Upon removal of needle cannula 16 from the patient, actuator 48 of latch 44 is depressed by squeezing actuator 46 relative to dorsal fin 40. This squeezing rotates latch 44 relative to dorsal fin 40, and causes locking end 48 of latch 44 to disengage from locking recess 52 of dorsal fin 50 on shield 20. As a result, spring 22 propels shield 20 distally and into shielding engagement with needle cannula 16. As shown in FIG. 2, shield 20 includes a plurality of proximally and outwardly extending resilient fingers 54. Resilient fingers 54 are biased inwardly when shield 20 is within outer wall 38 of hub 14. However, fingers 54 resiliently deflect outwardly and into an unbiased condition after shield 20 moves into shielding engagement around needle cannula 16. In this position, fingers 54 prevent shield 20 from moving proximally into a condition where needle cannula 16 is re-exposed. Interengageable flanges on distal end 34 of hub 14 and on the proximal end of shield 20 prevent complete separation of shield 20 from hub 14 substantially as in the previously described embodiments.

What is claimed is:

1. A needle assembly for a blood collection set comprising:
    a hub having opposed proximal and distal ends and a passage extending therebetween, said outer tube of said hub comprising at least one fin projecting outwardly on the hub for gripping said needle assembly;
    a needle cannula having a proximal end rigidly connected to said distal end of said hub, said needle cannula further having a distal end and a lumen extending between said ends, said lumen being in fluid communication with said passage through said hub;
    a shield telescoped over at least a portion of said needle cannula, said shield being movable from a proximal position where said distal end of said needle cannula is exposed to a distal position where said distal end of said needle cannula is shielded;
    a spring captured between portions of said hub and said shield and being operative for propelling said shield into said distal position relative to said hub and said needle cannula; and
    a resiliently deflectable latch formed on said fin of said hub, said latch having a locking projection releasably engaging a portion of said shield, an actuator being formed on said latch at a location spaced from the locking projection, said actuator being configured and disposed for deflecting said locking projection for selectively releasing said retainer from said shield and enabling said spring to propel said shield to said distal position.

2. The needle assembly of claim 1, wherein said shield includes a fin aligned with said fin on said hub, said fin on said shield including a retaining recess formed therein, said locking projection of said latch being releasably engageable with said retaining recess of said fin of said shield.

3. The needle assembly of claim 1, further comprising a plurality of proximally and outwardly directed resilient fingers formed on said shield, said fingers engaging said distal end of said hub when said shield is in said distal position for preventing re-exposure of said needle cannula.

4. The needle assembly of claim 1, wherein the hub further comprises a pair of wings extending outwardly therefrom, said wings being equally angularly spaced from said fin of said hub.

5. The needle assembly of claim 1, wherein the proximal end of the hub is configured for engaging a flexible tube for providing fluid communication between said flexible tube and said needle cannula.

6. The needle assembly of claim 1, wherein the hub includes inner and outer tubes extending between said proximal and distal ends, the inner and outer tubes being connected to one another at said proximal end of the hub, a cylindrical space being defined between said inner and outer tubes of said hubs at locations extending proximally from the distal end of said hub, a portion of said shield being releasably engaged in said cylindrical space between said inner and outer tubes of said hub when said shield is in said proximal position.

7. The needle assembly of claim 6, wherein the shield includes a proximal end having a plurality of resiliently deflectable fingers, said fingers being deflected inwardly and disposed in said cylindrical space between said inner and outer tubes of said hub when said shield is in said proximal position, said fingers expanding radially outwardly when said shield is released from said proximal position for preventing proximal movement of the shield and re-exposure of said needle cannula.

* * * * *